United States Patent
Steeves et al.

(10) Patent No.: US 8,114,679 B2
(45) Date of Patent: Feb. 14, 2012

(54) OPTICAL BIOSENSING PLATFORM UTILIZING NANOCRYSTALLINE ZINC OXIDE

(75) Inventors: Diane M. Steeves, Franklin, MA (US); Jason W. Soares, Shrewsbury, MA (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 12/079,088

(22) Filed: Feb. 11, 2008

(65) Prior Publication Data
US 2009/0068755 A1    Mar. 12, 2009

Related U.S. Application Data

(60) Provisional application No. 60/994,160, filed on Sep. 11, 2007.

(51) Int. Cl.
*G01N 21/76* (2006.01)
(52) U.S. Cl. ......... 436/172; 257/252; 257/253; 257/414
(58) Field of Classification Search .................. None
See application file for complete search history.

(56) References Cited

U.S. PATENT DOCUMENTS

| 5,833,603 A | 11/1998 | Kovacs et al. |
| 6,699,316 B2 | 3/2004 | Marx et al. |
| 6,914,279 B2 | 7/2005 | Lu et al. |

OTHER PUBLICATIONS

Janssen, Dimitri, et al. Static solvent contact angle measuements, surface free energy and wettability determination of various self-assembled monolayers on silicon dioxide, 2006, Thin Solid Films, vol. 515, pp. 1433-1438.*
Dorfman, Adam, et al. Highly Sensitive biomolecular Fluorescence Detection Using Nanoscale ZnO Platforms, 2006, Langmuir, vol. 22, pp. 4890-4895.*
Monticone, S., et al., Complex Nature of the UV and Visible Fluorescence of Colloidal ZnO Nanoparticles, 1998, Journal of Physical Chemistry B, vol. 102, pp. 2854-2862.*
Soares, Jason W., et al., Surface modification of nanocrystalline zinc oxide for bio-sensing applications, 2006, Proc. of SPIE, vol. 6370, pp. 637011-1-637011-9.*

* cited by examiner

*Primary Examiner* — Yelena G Gakh
*Assistant Examiner* — Robert Xu
(74) *Attorney, Agent, or Firm* — Roger C. Phillips

(57) ABSTRACT

An optical biosensing platform for the real-time detection of the occurrence of a binding event, the optical biosensing platform comprising a nanocrystalline zinc oxide (nano-ZnO) substrate having a surface and being capable of emitting photoluminescence and a surface modifier formed integral with at least a portion of the surface of the nano-ZnO substrate, wherein the surface modifier is capable of binding to a biomolecule and wherein when the surface modifier binds with a biomolecule, a change is induced in the emitted photoluminescent properties of the nano-ZnO substrate, thereby enabling the detection of a binding event.

7 Claims, 7 Drawing Sheets

OPTICAL BIOSENSING PLATFORM UTILIZING NANOCRYSTALLINE ZINC OXIDE

CROSS REFERENCE TO RELATED APPLICATIONS

This application claims benefit of prior filed U.S. Provisional Patent Application Entiled "A Novel Approach of Using Nanocrystalline Zinc Oxide as an Optical Sensing Platform", Ser. No. 60/994,160, filed Sep. 11, 2007, and fully incorporated by reference herein.

STATEMENT OF GOVERNMENT INTEREST

The invention described herein may be manufactured and used by the U.S. Government for governmental purposes without the payment of any royalty thereon.

BACKGROUND OF THE INVENTION

1. Field of the Invention

The invention relates to a novel optical biosensing platform in general, and more particularly to an optical biosensing platform utilizing surface-modified nanocrystalline zinc oxide for the real-time detection of the occurrence of a binding event.

2. Description of the Prior Art

There are various optical biosensing platforms which are currently used to identify the occurrence of a binding event between biomolecules, e.g., between a receptor and a ligand.

One of these optical biosensing platforms combines the use of biomolecules and a biosensing substrate (e.g., a high surface area material), wherein the biosensing substrate is used to provide an optical signal resulting from the binding event. For example, porous silicon cast films have been used as biosensing substrates because of their ease of fabrication, inherent optical properties, porosity, and the ability to chemically functionalize silicon. More particularly, the porosity of the silicon substrate increases the available surface-area for the attachment of receptors.

The surface of porous silicon cast films can be chemically-derivatized to introduce various reactive groups (e.g., —$NH_2$, —COOH, —SH, etc.) in order to enable covalent immobilization of biomolecules. These immobilization techniques retain the activity and long-term stability of the biomolecules. By way of example but not limitation, biomolecules, such as enzymes, DNA, proteins, cells, and lipopolysaccharide components, etc. have all been successfully immobilized to porous silicon for use in the capture of specific analytes. When using porous silicon substrates, the occurrence of specific binding events is measured and/or identified by variations in refractive index, shifts in reflectance, ellipsometry, and/or photoluminescence, etc.

While porous silicon may be used as an optical biosensing platform, its use is hindered by the need to tailor the pore size of the silicon in order to accommodate a specific receptor-ligand pair of interest. In addition to the time required to prepare a specific pore size and platform for each receptor-ligand pair of interest, the steric hindrance imposed by the porous structure limits the usable surface area available for receptor-ligand pair binding. Together, these disadvantages significantly complicate the process of using porous silicon as an optical biosensing platform.

In addition to silicon substrate platforms, other techniques exist for optically detecting binding events. Some optical biosensing techniques, such as those associated with magnetic nanoparticles, utilize an indirect approach for detecting binding events. These techniques require labeling one or more of the biomolecules (e.g., receptors, ligands, etc.) with a fluorescent "reporter" tag molecule. Subsequently, the "tagged" biomolecule is passed through an appropriate optical reader in order to detect whether a binding event has occurred.

These techniques have numerous disadvantages including increased complexity, lengthy sample preparation techniques, time-consuming analysis, and limited sensitivity.

Accordingly, there is a need for an optical biosensing platform wherein the pore size does not need to be tailored for a specific receptor-ligand pair and which also overcomes the limitations associated with fluorescent tagging.

Nano-ZnO has the desirable qualities indicated above, e.g., large surface area, mechanical and thermal stability, and an inherent photoluminescence signal.

Nano-ZnO is presently used as a wide band gap semiconductor due to its potential applications in the areas of photonics, electronics and sensors. For example, nano-ZnO has been used as a gas sensor by monitoring changes in its electrical resistivity.

In addition, nano-ZnO has been used as a biosensor platform wherein the binding of a target analyte is detected using a variety of techniques. These include obtaining electrical measurements, monitoring changes in conductivity, using quantum dots, incorporating optical dyes and/or measuring changes in the optical density of ZnO.

The photoluminescence signal inherent to as-grown ZnO nanostructures (FIG. 1) consists of two emission peaks. One of the peaks is emitted within the ultraviolet (UV) region and the other peak is emitted within the visible region of the electromagnetic spectrum (FIG. 2). The presence of these two distinct photoluminescent (PL) emission bands (i.e., ultraviolet and visible) make it desirable to use nano-ZnO as a potential real-time optical biosensing platform. More particularly, a surface binding event induces a change (e.g., in emission intensities, in emission maxima shifts and/or in peak proportionalities, etc.) within the inherent photoluminescent (PL) properties of nano-ZnO. This change can then be used to detect the binding event of a specific target ligand to the surface of the nano-ZnO. Thus, nano-ZnO eliminates the need for fluorescent labeling and provides an opportunity to detect real-time binding events through UV or visible peak emission intensity changes, emission-maximum shifts, and peak proportionality changes.

However, in order to detect the binding of a specific target ligand, the surface of the nano-ZnO must first be functionalized with an appropriate receptor. Moreover, through the process of functionalizing the nano-ZnO surface, it is possible that the inherent photoluminescent (PL) properties of nano-ZnO may be adversely affected. By way of example, previous studies have shown that surface alterations to nano-ZnO generally stabilize the ultraviolet (UV) emission but typically diminish the visible emission. This results in the loss of the versatility of the two distinct inherent emission peaks of nano-ZnO, and functionality as an optical biosensor platform is thereby significantly decreased. Furthermore, those surface-altered ZnO nanostructures have not introduced any level of chemical functionality and, therefore, are not satisfactory techniques in the development of nano-ZnO-based optical biosensors.

There is thus a need for an optical biosensor platform which remedies the aforementioned shortcomings of the current platforms in use.

SUMMARY OF THE INVENTION

An object of the invention is, therefore, to provide an optical biosensor platform which addresses and overcomes the limitations associated with the prior art.

These and other objects are addressed by the provision and use of the present invention, which provides a novel optical biosensing platform utilizing surface-modified nanocrystalline ZnO.

In one form of the present invention, there is provided an optical biosensing platform for the real-time detection of the occurrence of a binding event, the optical biosensing platform comprising:

a nanocrystalline zinc oxide (nano-ZnO) substrate having a surface and being capable of emitting photoluminescence; and a surface modifier formed integral with at least a portion of the surface of the nano-ZnO substrate, wherein the surface modifier is capable of binding to a biomolecule;

wherein when the surface modifier binds with a biomolecule, a change is induced in the emitted photoluminescent properties of the nano-ZnO substrate, thereby enabling the detection of a binding event.

In another form of the present invention, there is provided a method for detecting the occurrence of a binding event, the method comprising:

providing an optical biosensing platform comprising:
a nanocrystalline zinc oxide (nano-ZnO) substrate having a surface and being capable of emitting photoluminescence; and
a surface modifier formed integral with at least a portion of the surface of the nano-ZnO substrate, wherein the surface modifier is capable of binding to a specific biomolecule and further wherein when the surface modifier binds with a biomolecule, a change is induced in the emitted photoluminescent properties of the nano-ZnO substrate;

providing a sample which potentially contains at least one biomolecule capable of binding with the surface modifier; and observing the nano-ZnO substrate to determine whether a change in the photoluminescent properties of nano-ZnO substrate has been induced, thereby enabling the detection of a binding event.

In another form of the present invention, there is provided a method for manufacturing an optical biosensing platform for the real-time detection of the occurrence of a binding event, the method comprising:

providing a nanocrystalline zinc oxide (nano-ZnO) substrate having a surface and being capable of emitting photoluminescence; and integrating the surface modifier with at least a portion of the surface of the nano-ZnO substrate, wherein the surface modifier is capable of binding to a specific biomolecule.

The above and other features of the invention, including various novel details of construction and combinations of parts, will now be more particularly described with reference to the accompanying drawings and pointed out in the claims. It will be understood that the optical biosensing platform embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENTS

The present invention comprises an optical biosensing platform utilizing surface-modified nanocrystalline zinc oxide for the real-time detection of the occurrence of a binding event.

Figure 1:
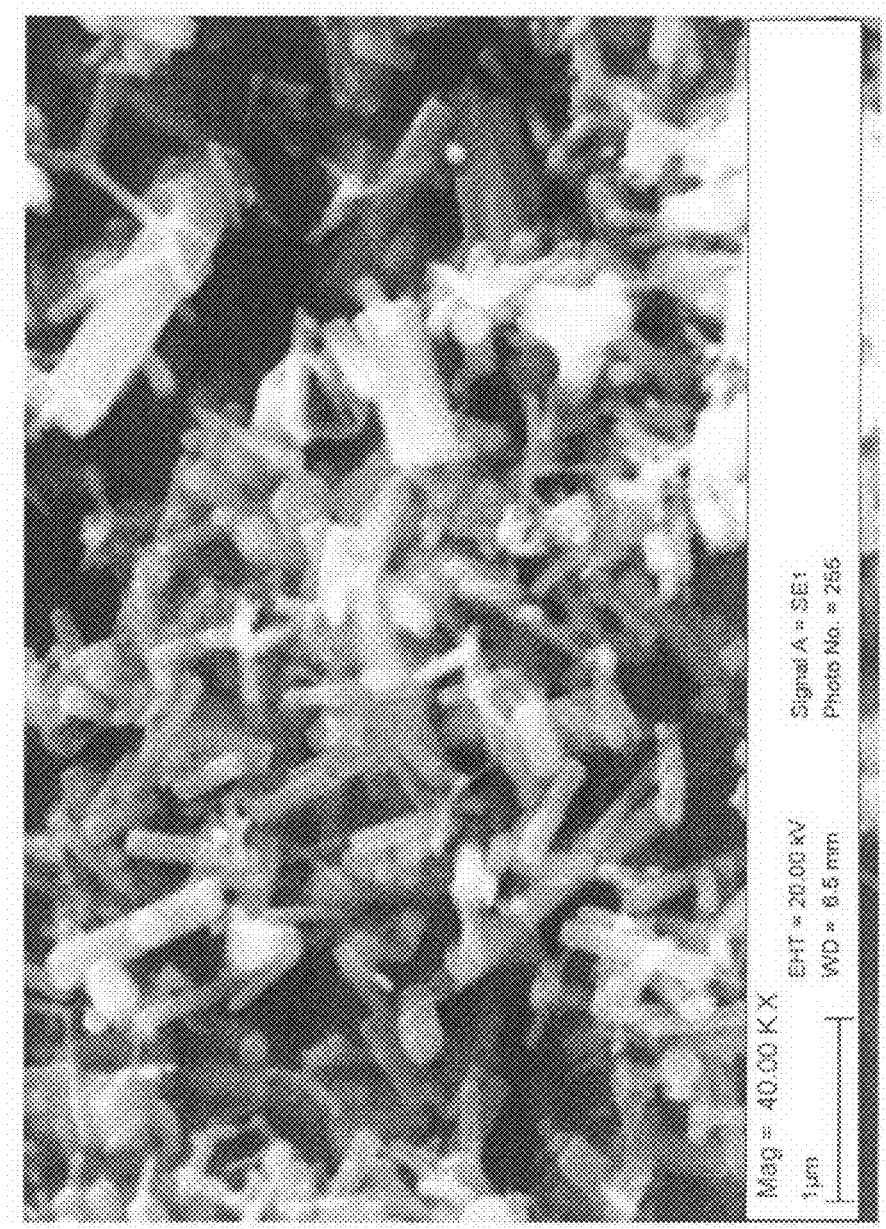
FIG. 1 is a scanning electron micrograph (SEM) image of nanocrystalline zinc oxide, in the form of nanorods ranging from 10 nm to 100 nm.
Figure 2:
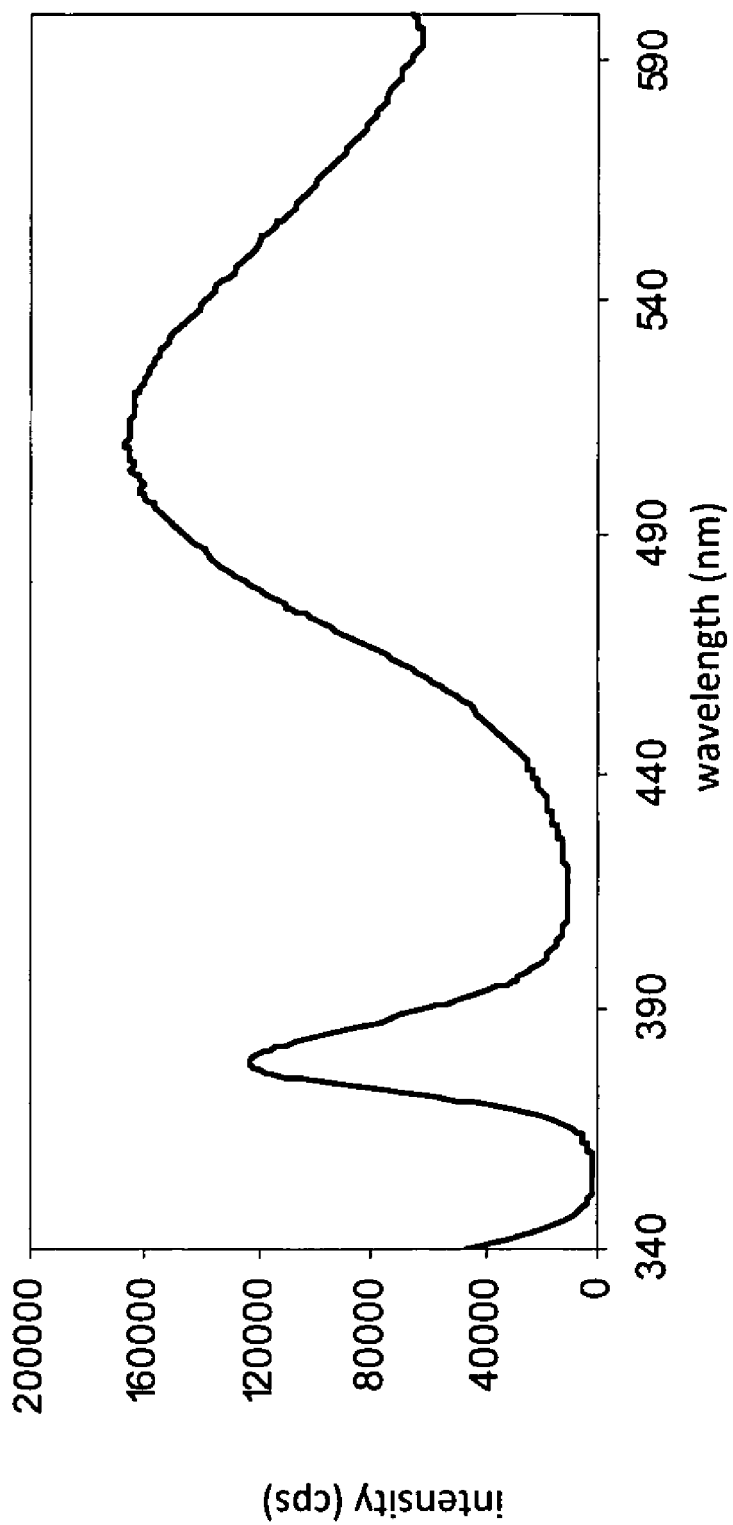
FIG. 2 illustrates the inherent photoluminescence of ZnO nanorods.
Figure 3:
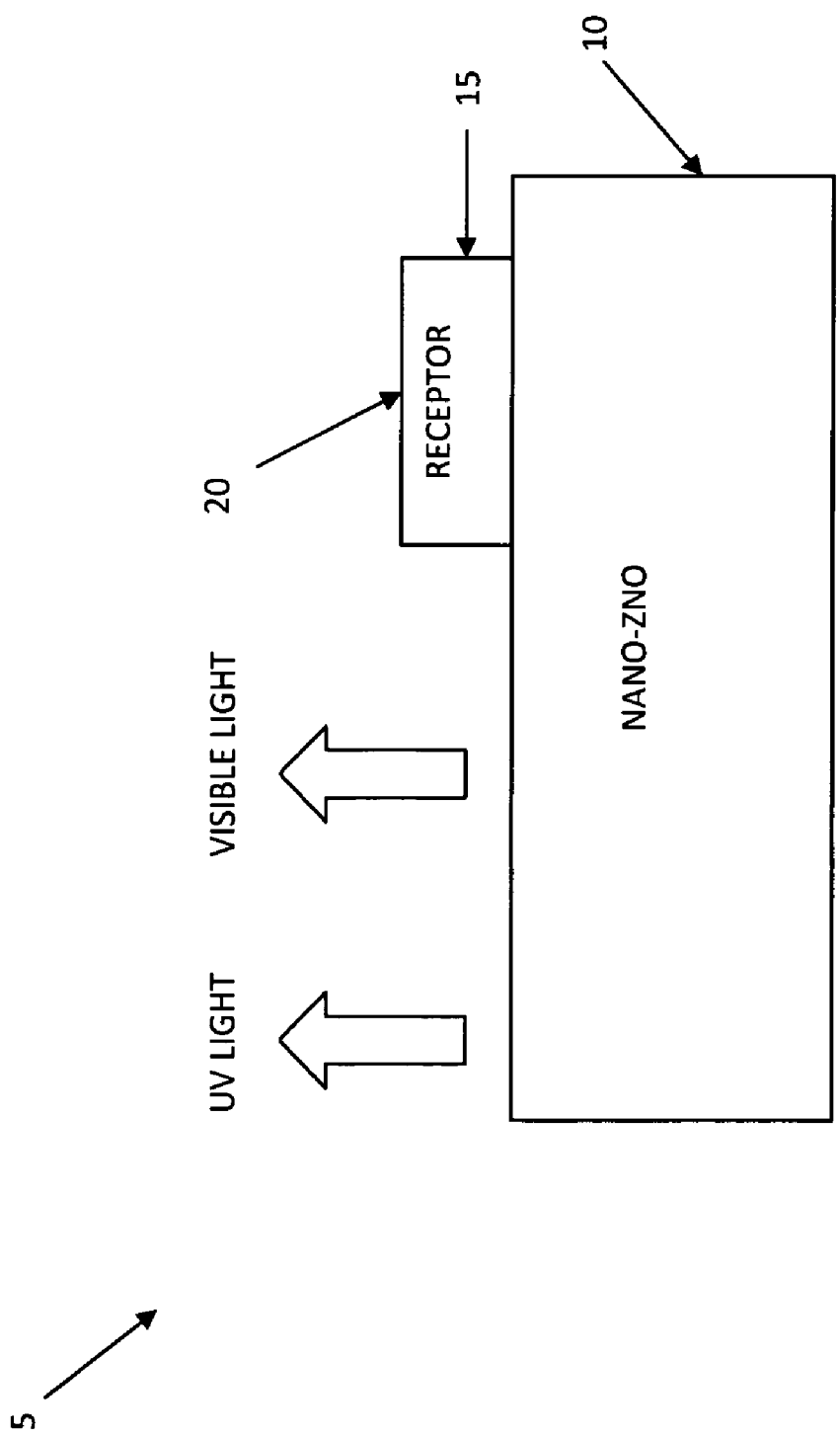
FIG. 3 illustrates a surface-modified nano-ZnO optical biosensor platform formed in accordance with the present invention.

Looking now at FIG. 3, in one form of the present invention, optical biosensing platform 5 comprises a nano-ZnO substrate 10 and a receptor 15, wherein receptor 15 is formed integral with the surface of nano-ZnO substrate 10, thereby creating a surface-modified nano-ZnO substrate.

The surface-modified nanocrystalline zinc oxide (nano-ZnO) substrate of the present invention provides surface functionalization (i.e., a receptor-ligand binding site 20) while still maintaining the inherent bimodal photoluminescent (PL) properties of zinc oxide.

Significantly, the present invention utilizes covalent surface modification to achieve the desired chemical functionality needed for subsequent biomolecular and/or chemical attachment. The surface modifiers are chosen to covalently attach specific molecular recognition elements (e.g., receptors) which allow for the binding of particular target analytes or ligands. By way of example but not limitation, the surface modifiers may attach antibodies, peptides, aptamers, DNA, enzymes, proteins, cells, lipopolysaccharides, etc. This provides real-time sensing based upon detecting induced changes, after ligand binding, within the inherent photoluminescence emission peaks, without the need to use secondary fluorescent labels or other chemical processes.

Figure 4:
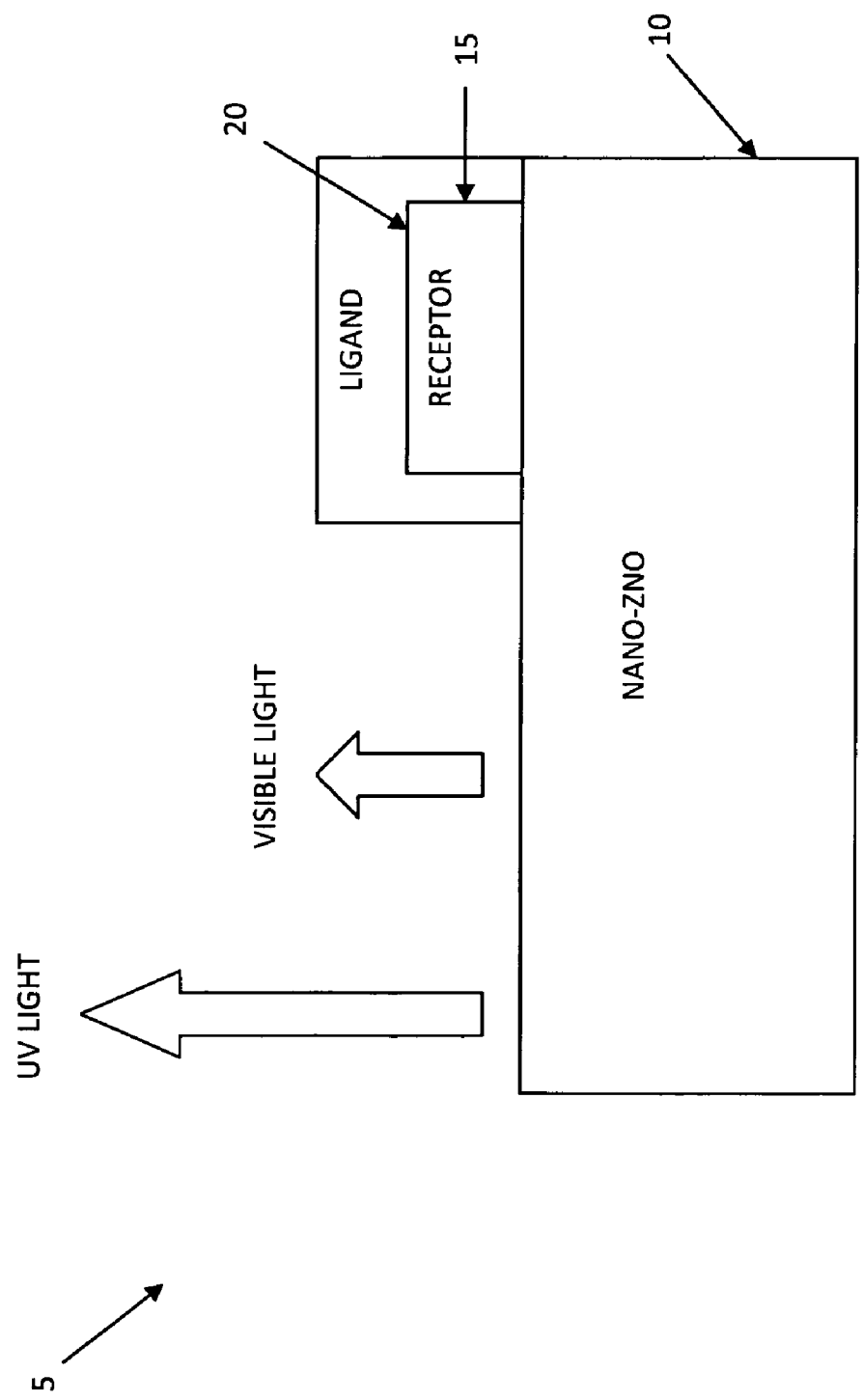
FIG. 4 illustrates a surface-modified optical nano-ZnO biosensor platform optically emitting photoluminescence after the occurrence of a binding event.

In a preferred embodiment, the present invention utilizes ZnO nanopowders which have (i) a wide band gap material with a high exciton binding energy (e.g., 60 meV), (ii) a large surface area for biological and/or chemical functionalization, and (iii) an inherent ability to co-generate two photoluminescence emission peaks. As stated above, one of the two photoluminescence emission peaks is located within the ultraviolet (UV) spectrum, due to near band edge emission and the other photoluminescence emission peak is located within the visible (green) region, due to oxygen vacancies caused by crystalline defects. Since a binding event will induce a change in the emission of the inherent photoluminescent (PL) spectrum of the ZnO nanopowder, it is possible to detect this change, and therefore the presence of a surface binding event. See FIG. 4.

Figure 5:
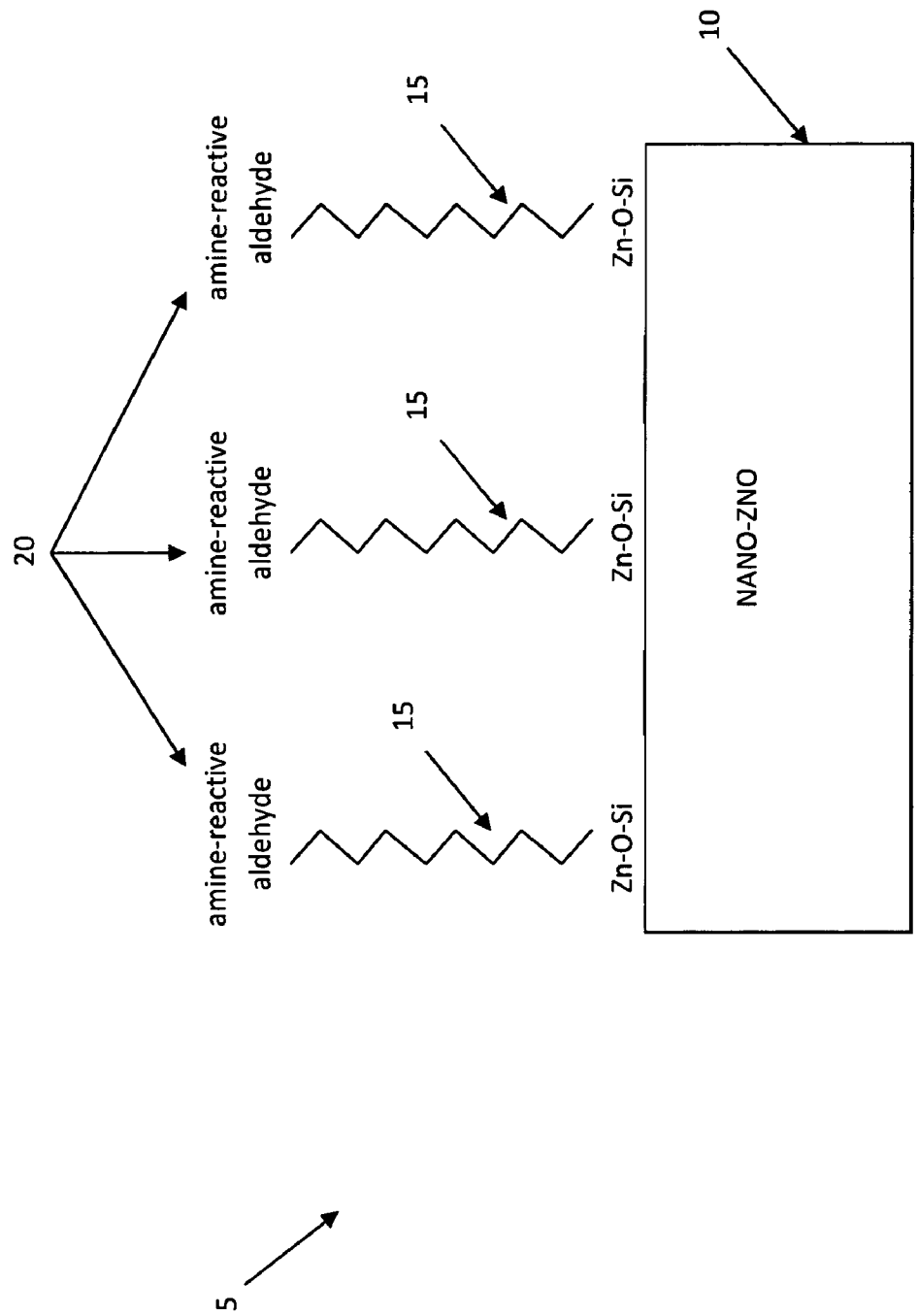
FIG. 5 illustrates an exemplary form of a surface-modified nano-ZnO optical biosensor platform formed in accordance with the present invention.

In the preferred embodiment, the nano-ZnO can be derivatized with a variety of surface modifiers in order to obtain the desired chemical reactivity for subsequent biomolecule covalent attachment. One example of a surface modifier which can be used in accordance with the present invention is a silane cross-linking agent, e.g., triethoxysilylundecanal. In this embodiment, and looking now at FIG. 5, the silane agent creates a Zn—O—Si bond at the surface of the ZnO nanopowder and introduces an amine-reactive aldehyde group at the other end of a 10-carbon spacer. The amine-reactive aldehyde group introduces a chemical functionality that allows coupling of biomolecules containing primary amino groups (e.g., a fluorescent dye hydrazide-derivative, biotin, peptides, etc.) to the surface of the ZnO.

In order to create the Zn—O—Si bond at the surface of the ZnO nanopowder an aqueous alcohol deposition technique may be used to provide for simultaneous surface hydrolysis and organosilane condensation steps.

In addition to the silane linker discussed above, which incorporates an amine-reactive aldehyde, other linkers such as, but not limited to, different organosilane linkers (e.g., 3-mercaptopropyltriethoxysilane) and/or isocyanate-containing molecules (e.g., N-(-p-maleimidophenyl) isocyanate) may be available to introduce alternative reactive groups. This could include multiplexing through the deposition of several linkers at one time to introduce multiple reactive groups and to provide supplementary attachment sites to bind a series of target biomolecules.

The inherent optical responses of the surface-modified nano-ZnO can then be obtained by known techniques and converted into a digital readout for real-time detection of biological or chemical threats.

As stated above, the surface functionalization (i.e., surface modification) of nano-ZnO induces a change in the photoluminescent spectrum of nano-ZnO, specifically to the ultraviolet (UV) emission peak. More particularly, the cross-linking agent causes a stable and reproducible enhancement of ultraviolet (UV) emission which can be as high as 3 times greater than the un-modified nano-ZnO material. More importantly, and in contrast to the prior art, this enhancement is made while still retaining the inherent visible emission intensity of the nano-ZnO. This has not previously been achieved in a post-nanocrystal growth modification process.

In the preferred embodiment, and as shown in FIG. 3, the surface-modified nanocrystalline zinc oxide of the present invention is modified on the surface and not within a cavity. This avoids pore-size complications, such as those encountered when using the porous silicon substrates of the prior art.

It is important to note that, since nano-ZnO possesses two inherent PL emission peaks, i.e., one in the UV region and one in the visible region, there is a greater opportunity for a surface binding event to induce emission intensity changes, emission-maximum shifts, and peak intensity proportionality changes than there is for materials that possess only one photoluminescent (PL) peak, or than those materials which must be labeled with unstable fluorescent taggants.

Additionally, due to the inherent photoluminescent (PL) properties of nanocrystalline ZnO structures, the optical biosensing platform of the present invention can be probed via optical characterization techniques for direct detection of a binding event. This is in contrast to the indirect detection techniques of the prior art, which require labeling with photoreactive moieties. The present invention thus avoids the increased complexity and instability associated with sample preparation and photo-instability of fluorescent dyes which are required in the indirect, labeling and detection techniques of the prior art.

Another method of probing changes in the inherent photoluminescent (PL) properties of nano-ZnO involves the measurement of photoluminescent (PL) lifetimes. Whereas photoluminescence (PL) spectroscopic measurements represent a composite photoluminescence (PL) response, lifetime measurements represent individual electronic events, which can be influenced by the immediate environment of the nano-ZnO, and hence may be an alternative approach to detecting binding events.

By way of example but not limitation, the ZnO nanocystals may also be probed with lasing and diffraction techniques for detecting induced optical changes. More particularly, ZnO nanocrystals have been shown to exhibit room temperature lasing capabilities. The lasing action of the ZnO is due to resonant cavities formed by multiple scattering and interference events. Light becomes confined in these resonant cavity regions, resulting in recurrent scattering, which then provides coherent feedback in closed loop paths, inducing lasing in the material. Since lasing ability of the crystals has been correlated to particle size, binding of recognition elements to the ZnO may induce changes in the lasing characteristics of the nanocrystals. Furthermore, investigation of diffraction patterns may be possible since particle size will increase upon a binding event, which can cause changes to the baseline white light diffraction. Both lasing and diffraction techniques would be best served by an aligned zinc oxide nanoarray.

In addition to the foregoing, the nano-ZnO optical biosensing platform of the present invention can provide enhanced sensitivity over current sensor platforms as well as a durable, stable, reagent-less device. This may result in real time chemical-biological (CB) detection with a reduction in the use of consumables, reduced footprint, and elimination of lengthy sample preparation. The attachment of multiple molecular recognition elements to the powders could lead to unique shifts in inherent photoluminescent spectra to not only detect the presence of pathogens but also to provide pathogen identification.

Potential benefits for the military could be a sensor device capable of generating a real time signal in a hand-held or integrated textile platform. The present invention may also be significant to Homeland Defense initiatives with emphasis on soldier food and/or water quality and safety.

The optical biosensing ZnO nanocrystals of the present invention may be used in a variety of applications. The tailoring of nano-ZnO surface chemistries may also allow for the incorporation of nano-ZnO into various electro-optical devices of interest to the military, such as short wavelength light emitting diodes, diode lasers, and optical sensors, which may be operative and stable in a variety of environments.

In summary, through the introduction of chemical functionality and retention of reactivity, the present invention creates a platform for forming biomolecular complexes on the nano-ZnO surface. The optically responsive biosensing platform of the present invention can serve as a template for immobilizing biomolecular recognition elements (MREs), including antibodies, aptamers, enzymes, peptides, etc. Although the silane linker discussed herein introduced an amine-reactive aldehyde, other linkers could also be employed to introduce alternative reactive groups. The introduction of other linkers could facilitate multiplexing through deposition of several different linkers at once to introduce multiple reactive groups and to immobilize MREs specific to a series of target ligands.

EXAMPLE 1

A heterobifunctional organosilane linker, 11-triethoxysilylundecanal was covalently attached to a nano-ZnO surface to introduce an amine-reactive functional group that would allow for biofunctionalization. Energy-dispersive X-ray spectroscopy (EDS) mapping of silicon atoms verified the presence of the cross-linking agent, and analysis confirmed a high concentration of Si on the nanorod surface. After organosilane surface modification, a series of washing steps ensured removal of any noncovalently attached silane agent. Because noncovalently attached Si atoms were removed during the washing process, EDS confirmed both the presence of the silane agent and covalent attachment. Analysis of the surface-modified nano-ZnO indicated that the complex is remarkably stable, with no silane dissociation after more than six months in storage at room temperature within a desiccator.

After surface modification, it must be verified that the amine-reactive group was stable and able to maintain reactive functionality in order to form biomolecule complexes (e.g., receptor-ligand pairs). To determine whether the aldehyde group was chemically reactive and available for subsequent biofunctionalization, a hydrazide derivative of a common fluorophore, i.e., Texas Red (TR) was used.

After derivatization, the nanopowders exhibited obvious and visible differences. The unmodified nano-ZnO remained white, while the surface-modified nano-ZnO was a deep purple, as expected with successful attachment of TR (see FIG. 6, inset).

Figure 6:
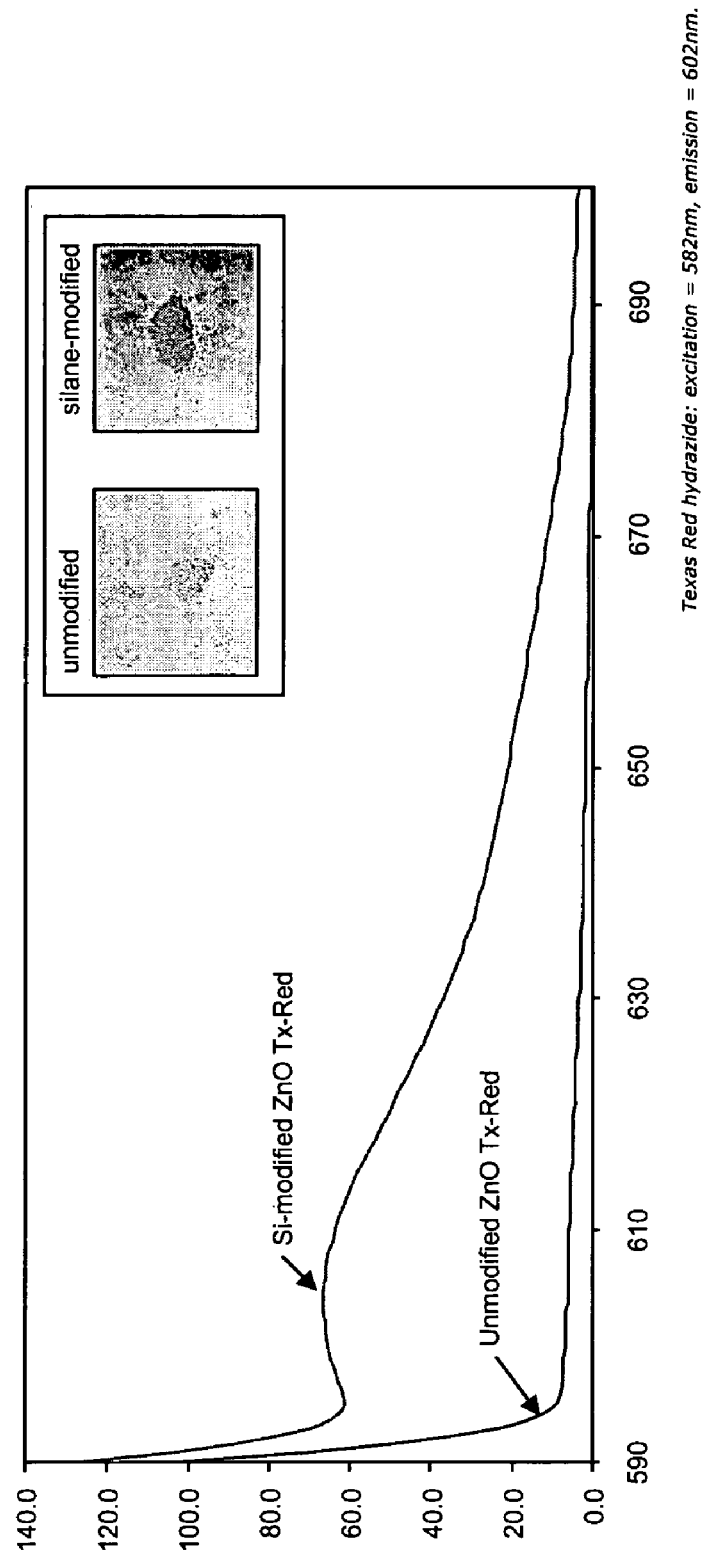
FIG. 6 illustrates the chemical reactivity of the covalently-attached surface modifier.

These powders, also investigated through fluorescence probing, clearly showed the presence of the silane linker on the surface-modified nano-ZnO. The unmodified nanopowder displayed minimal incorporation of TR, indicating that nonspecific binding was negligible (FIG. 6). Significantly, because the hydrazide form of TR is specifically designed for covalent attachment to amine-reactive aldehyde groups, these results illustrated that the chemically reactive functionality of the aldehyde, while in its immobilized state, was retained.

EXAMPLE 2

Organosilane Surface Modification. Nanocrystalline ZnO nanorods (Nanocerox, Inc.) with a mean particle size of 10-20 nm wide by 100-300 nm long, as determined by transmission electron microscopy (TEM), were dried overnight under vacuum at 200° C. before use. The nano-ZnO was suspended by means of sonication via a Branson Cell Disruptor in 95% ethanol/5% $H_2O$ at pH 5 (adjusted with acetic acid). The organosilane linker (11-triethoxysilylundecanal, Gelest, Inc.) was added, without purification, to achieve 1:2.5 w/w ZnO/silane and was allowed to react for 1 hour at 75° C. The powders were collected by filtration and washed extensively with 100% ethanol. The samples were cured at 110° C. for 10 minutes and stored in a desiccator.

Fourier Transform Infrared Spectroscopy (FTIR) Analysis Of Surface-Modified Nano-Zno. FTIR spectra of the powdered materials were acquired using a BioRad Fourier transform infrared spectrometer (model FTS-60A). Potassium bromide (KBr) pellets were prepared for FTIR analysis using 200 mg of KBr and 15 mg of sample. A background scan was performed using pure KBr and was automatically subtracted from the data. A total of 32 scans were averaged for each sample.

Optical Characterization. The photoluminescence spectra of the powdered materials were acquired using a Fluorolog 3 fluorescence spectrometer (Horiba Jobin Yvon, Inc.) equipped with a solid sample holder accessory at an excitation wavelength of 325 nm. Three scans were acquired and averaged together for each sample.

X-ray photoelectron spectroscopy (XPS) Analysis. Samples for XPS analysis were prepared by suspending 60 mg of the unmodified nano-ZnO or the silane-modified nano-ZnO in 30 mL of the aqueous ethanol solution and sonicating for 3 minutes using a Branson Cell Disruptor. The resulting dispersion was poured over a small copper coupon (1 $cm^2$, cleaned with dilute hydrochloric acid and distilled water) in a Gooch crucible. Copper coupons were used as a means to fix the powders and to minimize surface charging that may occur as a result of uncompensated electron ejection during analysis. The solution was allowed to evaporate/drain through the crucible overnight at room temperature. This procedure resulted in a uniform coating of the nano-ZnO powder onto the copper coupons. The metal substrates were mounted as is on sample stubs using conducting silver paint on the back side of the substrate holder. The XPS spectra were acquired using 100 W Al Kα X-rays.

Figure 7:
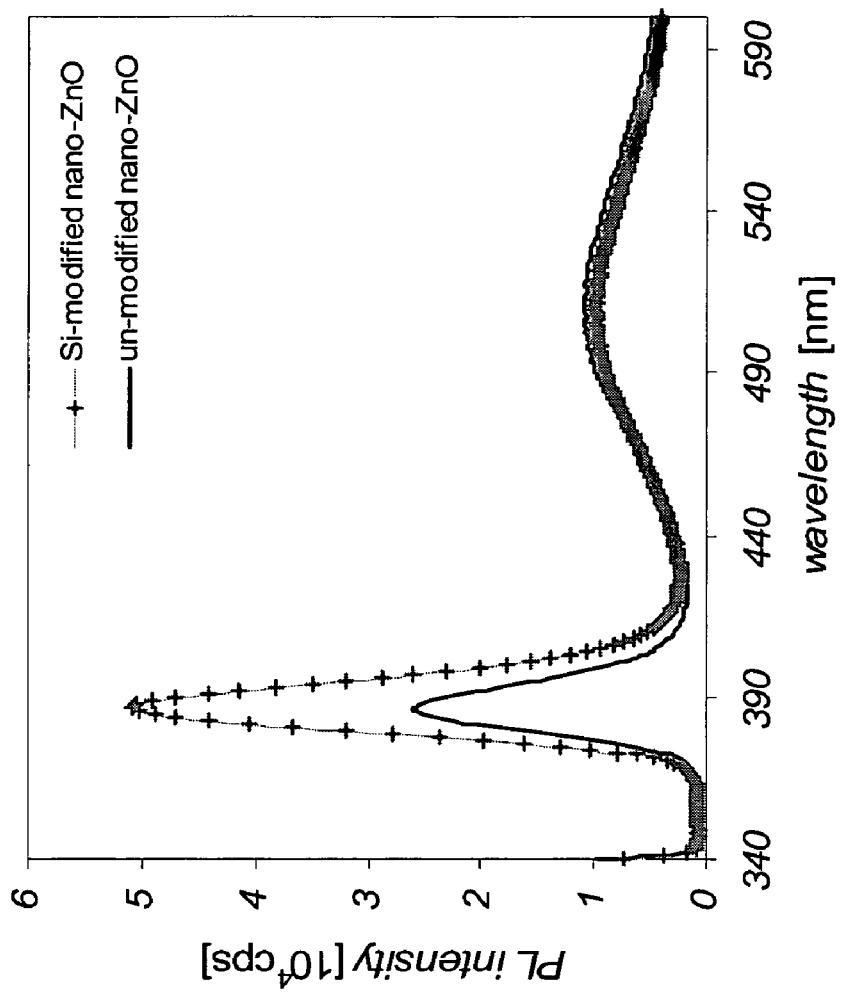
FIG. 7. illustrates the change in the intensity of the emitted photoluminescence between an unmodified nano-ZnO and a surface modified nano-ZnO.

The presence of the surface-attached cross-linking agent was verified through FTIR analysis. XPS analyses demonstrated covalent attachment of the surface-modifier. In addition, as shown in FIG. 7, the intensity of the emitted photoluminescence of the surface-modified nano-ZnO was significantly higher than the intensity of the emitted photoluminescence of the unmodified nano-ZnO.

It is to be understood that the present invention is by no means limited to the particular construction herein disclosed and/or shown in the drawings, but also comprises any modification or equivalent within the scope of the claims.

What is claimed is:

1. An optical biosensing platform for the real-time detection of the occurrence of a binding event, the optical biosensing platform comprising:
   a nanocrystalline zinc oxide (nano-ZnO) substrate having a surface and being capable of emitting photoluminescence, said photoluminescence comprising an inherent photoluminescence signal consisting of two emission peaks, a first peak being within an ultraviolet (UV) region of an electromagnetic spectrum, and a second peak being within a visible region of the spectrum; and
   a surface modifier being capable of binding to a biomolecule, said modifier formed integral with at least a portion of the surface of the nano-ZnO substrate, said surface modifier being chosen for attaching a specific receptor, said receptor for allowing the binding of a particular target biomolecule;
   wherein when the surface modifier binds with a said biomolecule, a change is induced in the emission of the inherent photoluminescent properties of the nano-ZnO substrate, said change occurring in at least one of the group consisting of emission intensities, emission maxima shifts and peak proportionalities of the inherent photoluminescent properties of the nano-ZnO substrate thereby enabling the detection of a binding event.

2. An optical biosensing platform according to claim 1 wherein the surface modifier comprises a silane cross-linking agent, said agent for creating a Zn—O—Si bond at the surface of the ZnO substrate, and for introducing a chemical functionality for allowing coupling of biomolecules.

3. An optical biosensing platform according to claim 2 wherein the silane cross-linking agent is triethoxysilylundecanal.

4. An optical biosensing platform according to claim 1 wherein the biomolecule comprises at least one of the group consisting of antibodies, peptides, aptamers, pathogens, DNA, enzymes, proteins, cells, lipopolysaccharides, fluorescent dye hydrazide-derivatives and biotin.

5. A method for detecting the occurrence of a binding event, the method comprising:
providing an optical biosensing platform comprising:
a nanocrystalline zinc oxide (nano-ZnO) substrate having a surface and being capable of emitting photoluminescence, said photoluminescence comprising an inherent photoluminescence signal consisting of two emission peaks, a first peak being within an ultraviolet (UV) region of an electromagnetic spectrum, and a second peak being within a visible region of the spectrum; and
a surface modifier being capable of binding to a specific biomolecule, said modifier formed integral with at least a portion of the surface of the nano-ZnO substrate, said surface modifier being chosen for attaching a specific receptor, said receptor for allowing the binding of a particular target biomolecule,
wherein when the surface modifier binds with a said biomolecule, a change is induced in the emission of the inherent photoluminescent properties of the nano-ZnO substrate, said change occurring in at least one of the group consisting of emission intensities, emission maxima shifts and peak proportionalities of the inherent photoluminescent properties of the nano-ZnO substrate;
providing a sample which potentially contains at least one biomolecule capable of binding with the surface modifier; and
observing the nano-ZnO substrate to determine whether a said change in said inherent photoluminescent properties of the nano-ZnO substrate has been induced, thereby enabling the detection of a binding event.

6. A method for manufacturing an optical biosensing platform for the real-time detection of the occurrence of a binding event, the method comprising:
providing a nanocrystalline zinc oxide (nano-ZnO) substrate having a surface and being capable of emitting photoluminescence; and
integrating a surface modifier with at least a portion of the surface of the nano-ZnO substrate, wherein the surface modifier is capable of binding to a specific biomolecule, and wherein said surface modifier comprises a silane cross-linking agent, said integrating comprising:
attaching the agent to the nano-ZnO surface for introducing a chemical reactive group for allowing biofunctionalization;
verifying a presence of the agent;
confirming a concentration of Si on the surface;
washing the surface for removing any noncovalently attached agent; and
verifying stability of the chemical reactive group for maintaining functionality for forming a biomolecule complex.

7. A method according to claim 6 wherein the silane cross-linking agent is triethoxysilylundecanal.

* * * * *